(12) United States Patent
Popilock

(10) Patent No.: US 6,661,865 B1
(45) Date of Patent: Dec. 9, 2003

(54) VARIABLE AXIAL SHIELDING FOR PET IMAGING

(75) Inventor: Robert M. Popilock, Hudson, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 281 days.

(21) Appl. No.: 09/790,142

(22) Filed: Feb. 21, 2001

(51) Int. Cl.$^7$ ................................................ A61B 6/00
(52) U.S. Cl. .............................. 378/19; 378/4; 600/427
(58) Field of Search ..................... 250/363.04, 363.1, 250/515.1, 505.1; 600/427, 407; 378/4, 154, 150, 153, 19

(56) References Cited

U.S. PATENT DOCUMENTS

| | | | |
|---|---|---|---|
| 2,818,510 A | 12/1957 | Verse | |
| 4,150,297 A | 4/1979 | Borggren | |
| 5,327,474 A | 7/1994 | Inoue et al. | |
| 5,391,877 A | 2/1995 | Marks | |
| 5,960,054 A | 9/1999 | Freeman et al. | |
| 6,031,888 A | 2/2000 | Ivan et al. | |
| 6,075,837 A | 6/2000 | Roos et al. | |
| 6,149,592 A | 11/2000 | Yanof et al. | |
| 6,205,347 B1 * | 3/2001 | Morgan et al. | 600/407 |
| 6,449,331 B1 * | 9/2002 | Nutt et al. | 378/19 |
| 6,490,476 B1 * | 12/2002 | Townsend et al. | 600/427 |

OTHER PUBLICATIONS

FischerImaging Product Data Sheet—Ceiling Suspended Imaging System.
Swissray Advertisement, *Medical Imaging*, vol. 12, No. 9, Sep. 1997.
Picker International, Orbitor HF Mobile C–Arms Product Data Sheet, 1994.
"Investigation of the Use of X–Ray CT Images for Attenuation Compensation in SPECT", K.J. LaCroix et al.
IEEE Transactions on Nuclear Science vol. 41, No. 6, Dec. 1994
"Object–Specific Attenuation Correction of SPECT With Correlated Dual–Energy X–Ray CT", Bruce H. Hasegawa et al.
IEEE Transactions on Nuclear Science, vol. 40, No. 4, Aug. 1993.

* cited by examiner

*Primary Examiner*—Craig E. Church
*Assistant Examiner*—Hoon Song
(74) *Attorney, Agent, or Firm*—Fay, Sharpe, Fagan, Minnich & McKee, LLP

(57) ABSTRACT

A diagnostic imaging system includes a rotating gantry (16) which defines a subject receiving aperture (18). A rotatable source of high energy penetrating radiation (20) and corresponding high energy radiation detector (26) are disposed across the subject receiving aperture (18). A plurality of nuclear detector heads (30a, 30b) are movably attached to the rotating gantry (16) in order to detect low energy radiation emitted by a radiopharmaceutical injected into the subject (12). Each of the nuclear detector heads (30a, 30b) within the system include a variable axial radiation shield (40a, 40b) disposed adjacent a radiation receiving face (38) on the detector head. The variable axial radiation shield (40a, 40b) includes a plurality of substantially parallel vanes (42) pivotally connected to each nuclear detector head (30a, 30b) for movement between an open configuration (FIG. 2) and a closed, radiation blocking configuration (FIG. 3).

15 Claims, 3 Drawing Sheets

VARIABLE AXIAL SHIELDING FOR PET IMAGING

BACKGROUND OF THE INVENTION

The present invention relates to the art of diagnostic imaging. It finds particular application in conjunction with multi-headed positron emission tomography (PET) scanners and will be described with particular reference thereto. However, it is to be appreciated that the present invention is also applicable to combined computed tomography (CT) and SPECT scanners as well as other diagnostic modes in which nuclear detector heads may become saturated and/or damaged from impermissibly high levels of radiation.

Diagnostic nuclear imaging is used to study a radionuclide distribution in a subject. Typically, one or more radiopharmaceutical or radioisotopes are injected into a subject. The radiopharmaceuticals are commonly injected into the subject's bloodstream for imaging the circulatory system or for imaging specific organs that absorb the injected radiopharmaceuticals. Sensitive scintillation crystal camera detector heads are placed adjacent to a surface of the subject to monitor and record emitted radiation. Typically, the detector heads are rotated or indexed around the subject in order to monitor the emitted radiation from a plurality of directions. In single photon emission computed tomography (SPECT), emission radiation is detected by one or more collimated detector heads. In positron emission tomography (PET), data collection is limited to emission radiation that is detected concurrently by a pair of oppositely disposed detector heads. The detected radiation data is then reconstructed into a three-dimensional image representation of the radiopharmaceutical distribution within the subject.

One of the problems with both PET and SPECT imaging techniques is that photon absorption and scatter by portions of the subject or subject support between the emitting radionuclide and the detector heads, distort the resultant image. In order to obtain more accurate SPECT and PET radiation attenuation measurements, a direct transmission radiation measurement is made using transmission computed tomography techniques. In the past, transmission radiation data was commonly acquired by placing a radioactive isotope line or point source opposite to a detector head, enabling the detector head to collect transmission data concurrently with the other two detector heads collecting emission data. This transmission data is then reconstructed into an image representation using conventional tomography algorithms. From this data, regional radiation attenuation properties of the subject, which are derived from the transmission computed tomography images, are used to correct or compensate for radiation attenuation in the emission data.

One PET scanning technique involves the injection of a radioisotope, which is selectively absorbed by tumors or other tissues of interest. The resulting PET images provide an accurate depiction of the location of the tumors in space. However, because only the radioactive isotope is imaged, the PET images provide no correlation between the image and the surrounding tissue. In order to coordinate the tumors with location in the patient, the same region of the subject is scanned with both the PET scanner and a computed tomography (CT) scanner. In the past, the PET and CT scanners were permanently mounted in a fixed relationship to each other. A patient was moved from one apparatus to the next. However, due to potential patient movement or repositioning between the CT scanner and the nuclear camera, this technique provided uncertainty in the alignment of the PET and CT images.

To eliminate the alignment problems associated with physically displaced imaging systems, it would be advantageous to mount the CT and nuclear imaging systems to a common gantry. However, nuclear detector heads are designed to detect very low levels of radiation. When exposed to higher levels of radiation, detector heads often saturate. The scintillation crystal on a detector head may be excited to such a high level that it continues to glow for an extended duration, which interferes with normal operation of the nuclear camera. In addition, very high radiation doses may even damage nuclear detector heads.

Although the x-rays of a CT scanner are intended to pass from the x-ray tube to the high energy x-ray detector, some of the x-rays are scattered in the patient or by scanner hardware. A significant number of radiation photons would find their way to the nuclear detector heads. Many of the gamma rays that reach the detector heads have been Compton scattered two, three, or more times in the patient. While these rays have lost significant amounts of energy, they are still well above the energy range of the detector head and may cause saturation of and/or damage to the detector heads.

The present invention contemplates a new and improved nuclear camera which overcomes the above-referenced problems and others.

SUMMARY OF THE INVENTION

In accordance with one aspect of the present invention, a diagnostic imaging system includes a stationary gantry which defines a subject receiving aperture and a source of penetrating radiation which transmits high energy radiation through a subject disposed in a subject receiving region. The radiation source is mounted for rotation around the stationary gantry subject receiving region. A radiation detector detects high energy radiation transmitted by the source after passage of the radiation through a subject in the subject receiving region. At least one nuclear detector head is mounted for rotation around the subject receiving region. The detector head detects low energy radiation emitted by a radiopharmaceutical injected into the subject. At least one reconstruction processor reconstructs high energy radiation received by the radiation detector and radiopharmaceutical radiation received by the nuclear detector head into volumetric image representations. A fusion processor combines the high energy and radiopharmaceutical radiation volumetric image representations together. A shield shields the nuclear detector heads from the high energy radiation.

In accordance with a more limited aspect of the present invention, each nuclear detector head includes a scintillation crystal which emits a short duration light scintillation in response to radiopharmaceutical radiation incident thereon and which glows emitting light for a longer duration in response to scattered high energy radiation. A plurality of opto-electrical elements are optically coupled to the scintillation crystal. The opto-electrical elements convert light received from the scintillation into a plurality of electrical output signals. A variable axial radiation shield is disposed adjacent the scintillator. The variable axial radiation shield shields the scintillation crystal from at least one of non-axial radiation events originating from the injected radiopharmaceutical and the high energy radiation originating from the source of penetrating radiation.

In accordance with a more limited aspect of the present invention, the variable axial radiation shield includes a plurality of substantially parallel vanes movably mounted adjacent the scintillation crystal.

In accordance with a more limited aspect of the present invention, the variable axial radiation shield includes a means for pivoting the plurality of substantially parallel vanes from an open orientation, which is substantially perpendicular to the scintillation crystal, to a closed orientation, which blocks radiation from reaching the scintillation crystal.

In accordance with another aspect of the present invention, a diagnostic imaging system includes a rotating gantry which defines a subject receiving aperture and a source of penetrating radiation and a corresponding detector means for generating a computed tomographic image representation of a subject disposed within the subject receiving aperture. A plurality of nuclear detector heads are rotatably mounted to the gantry, each detector head having a radiation receiving face and a variable radiation filter for selectively restricting and permitting radiation to strike the radiation receiving face. The variable radiation filter includes a plurality of vanes movably mounted across the radiation receiving face. In the diagnostic imaging system, a method of diagnostic imaging includes positioning the plurality of vanes of the variable radiation filter such that they block radiation from striking the radiation receiving face. Radiation from the radiation source is transmitted through the subject and toward the corresponding detector means positioned across the receiving subject aperture. The transmitted radiation is reconstructed into a volumetric image representation. A radiopharmaceutical is injected into the subject disposed within the subject receiving aperture. The plurality of vanes of the variable radiation filter are positioned such that radiation emitted by the radiopharmaceutical is receivable by the radiation receiving face. Radiation emitted by the radiopharmaceutical is detected and reconstructed with an emission image representation. The reconstructed volumetric and emission image representations are combined into a combined image representation.

In accordance with another aspect of the present invention, a detector head for use in a nuclear camera includes a scintillator which emits light in response to incident radiation. A plurality of opto-electrical elements, which are optically coupled to the scintillator, convert light received from the scintillator into a plurality of electrical output signals. A variable axial radiation shield, which is disposed adjacent the scintillator, is moveable between (i) an open configuration in which it collimates incident radiation and (ii) a closed configuration in which it blocks incident radiation from reaching the scintillator.

In accordance with a more limited aspect of the present invention, the variable axial radiation shield includes a plurality of vanes tiltably mounted adjacent the scintillator.

In accordance with a more limited aspect of the present invention, the variable axial radiation shield includes a means for tilting the plurality of vanes between at least an orientation substantially perpendicular to the scintillator in the open configuration and an orientation substantially parallel to the scintillator in the closed configuration.

One advantage of the present invention resides in the elimination of detector saturation due to scattered radiation from external radiation sources.

Another advantage of the present invention is that it facilitates combined CT/PET diagnostic imaging.

Another advantage of the present invention resides in the simplicity and ease of use.

Other benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
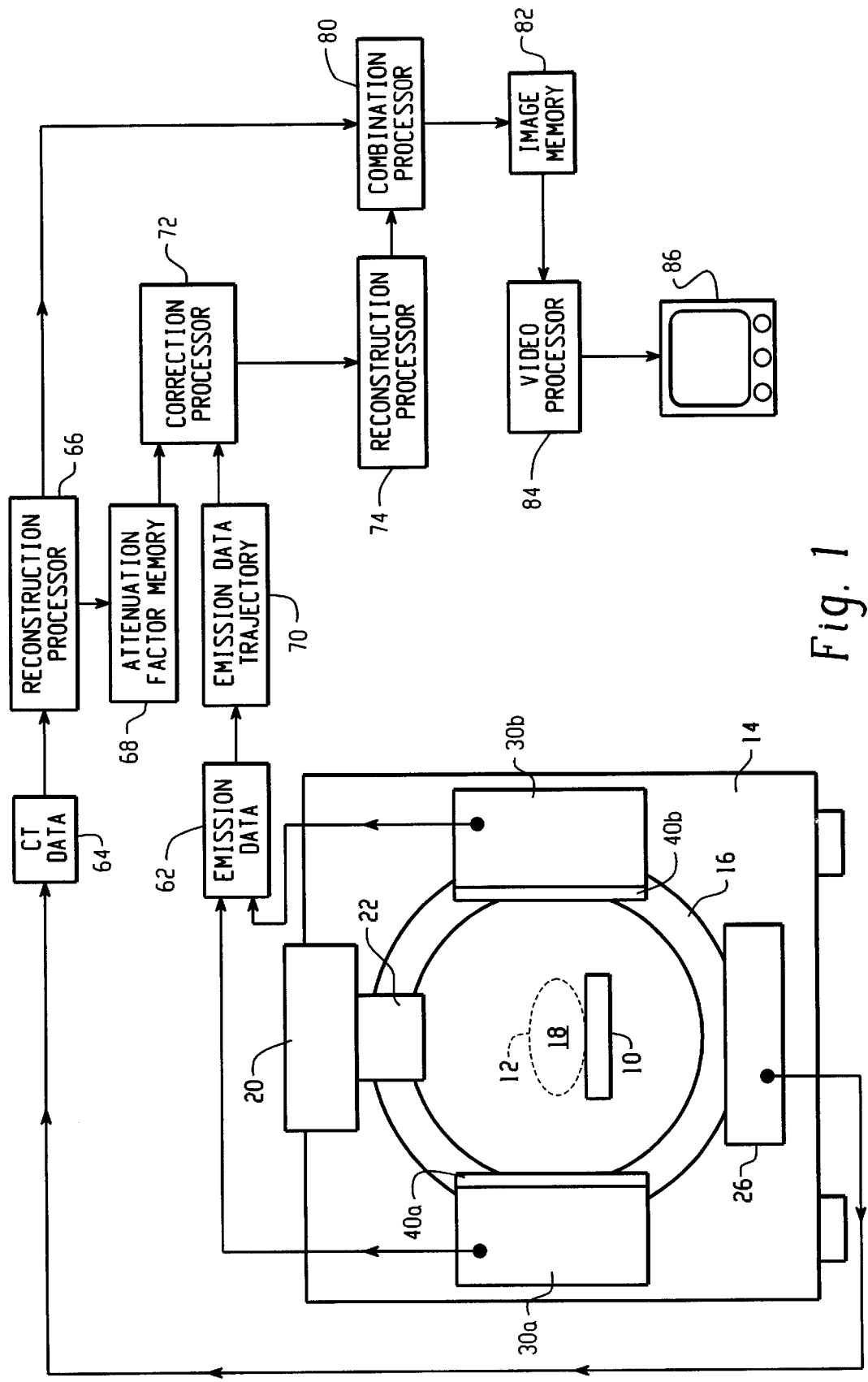
FIG. 1 is a diagrammatic illustration of a combined positron emission tomography (PET)/computerized tomographic (CT) diagnostic system in accordance with the present invention.

With reference to FIG. 1, a diagnostic imaging apparatus includes a subject support 10, such as a table or couch, which supports a subject 12 being examined and/or imaged. The subject 12 is injected with one or more radiopharmaceuticals or radioisotopes such that emission radiation is emitted therefrom. The subject support 10 is selectively height adjustable so as to center the subject at a desired height. A first or stationary gantry 14 rotatably supports at least one rotating gantry 16. The rotating gantry 16 defines a subject receiving aperture 18. The subject support 10 is advanced and/or retracted to achieve the desired positioning of the subject 12 within the subject receiving aperture 18.

An x-ray tube assembly 20 mounted on the rotating gantry 16 projects one or more beams of radiation through the subject receiving aperture 18. A collimator 22 collimates the radiation into one or more substantially parallel fan beams of selected thickness and spread or other selected beam cross section. An x-ray detector 26, such as a two-dimensional flat panel, high energy x-ray detector, is rotatably disposed on the rotating gantry across the subject receiving aperture 18 from the x-ray tube 20. Alternately, a ring of detectors are stationary mounted around the subject receiving aperture 18. optionally, another collimator is positioned adjacent the detectors to limit the receipt of radiation to the. selected cross section.

At least two nuclear detector heads 30a, 30b are moveably mounted to a rotating gantry, shown in FIG. 1 as the same rotating gantry 16 as the x-ray tube assembly. Mounting the x-ray tube assembly and the nuclear detector heads permits the region of interest to be imaged by both modalities without shifting the patient. Mounting the x-ray system and the nuclear heads to separate offset gantries simplifies achieving the different rotational speeds with which CT and nuclear cameras typically rotate. The detector heads 30a, 30b are radially adjustable to vary their spacing. In SPECT cameras, separate translation devices (not shown) translate the heads laterally and circumferentially.

Figure 2:
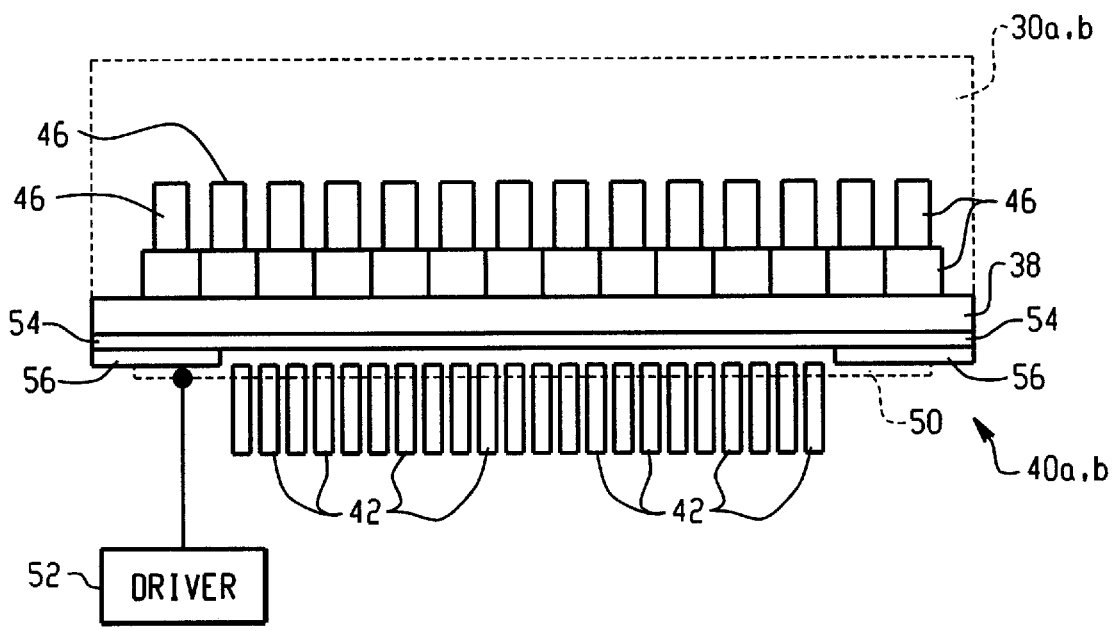
FIG. 2 is a diagrammatic illustration of a nuclear detector head employing a variable axial radiation shield in a radiation collimating mode in accordance with the present invention.

With reference to FIG. 2, and continuing reference to FIG. 1, each of the nuclear detector heads 30a, 30b has a radiation receiving face facing the subject receiving aperture 18. Each nuclear detector head includes a scintillation crystal 38, such as a large, doped sodium iodide crystal,.which emits a flash of light or photons in response to incident radiation. The nuclear detector heads 30a, 30b include mechanical collimators or variable axial radiation shields 30a, 30b, which are mounted on the radiation receiving faces of the detector heads. As is described more fully below, the variable axial radiation shields preferably include an array of lead or tungsten vanes 42, which restrict the nuclear detector heads from either receiving radiation not traveling along selected rays or completely shield the detector heads from receiving any radiation.

An array of photomultiplier tubes 46, or other optoelectrical elements, receive the light from the scintillation crystal 38 and convert it into electrical signals. A resolver circuit resolves the x, y-coordinates of each flash of light and the corresponding energy of the incident radiation. That is to say, radiation strikes the scintillation crystal 38 causing the scintillation crystal to scintillate, i.e., emit light photons in response to the incident radiation. The photons are received by the photomultiplier tubes 46 and the relative outputs of the photomultiplier tubes are processed and corrected to generate an output signal indicative of (i) a position coordinate on the detector head at which each radiation event is received, and (ii) an energy associated with each event.

In SPECT imaging applications, a projection image representation is defined by the radiation data received at each coordinate. In PET imaging applications, the detector head outputs are monitored for coincident radiation. From the position and orientation of the heads and the location on each head at which the coincident radiation was received, a ray between the peak detection points is calculated. This ray defines a line along which the radiation event occurred. The emission radiation data is then reconstructed into a volumetric image representation of the region of interest.

With continuing reference to FIG. 2, each axial filter/mechanical collimator 30a, 30b mounted on the nuclear detector heads 30a, 30b includes a plurality of substantially parallel vanes 42, which are pivotally connected to the nuclear detector head. The plurality of substantially parallel vanes serve as a variable axial radiation shield 30a, 30b. When the plurality of vanes are oriented substantially perpendicular to the scintillator or open, as shown in FIG. 2, the variable axial filter is in a radiation collimating mode, in which non-axial radiation events originating from the injected radiopharmaceutical are filtered. In other words, in this mode, the variable axial radiation shield serves as a filter or collimator, which limits the number of wide angle photon events that reach the scintillator. Artisans will appreciate that wide angle events are primarily characterized as random or scattered photons, also known as single events, which degrade image quality by decreasing contrast, adding positioning uncertainty, and possibly saturating detector electronics.

Figure 3:
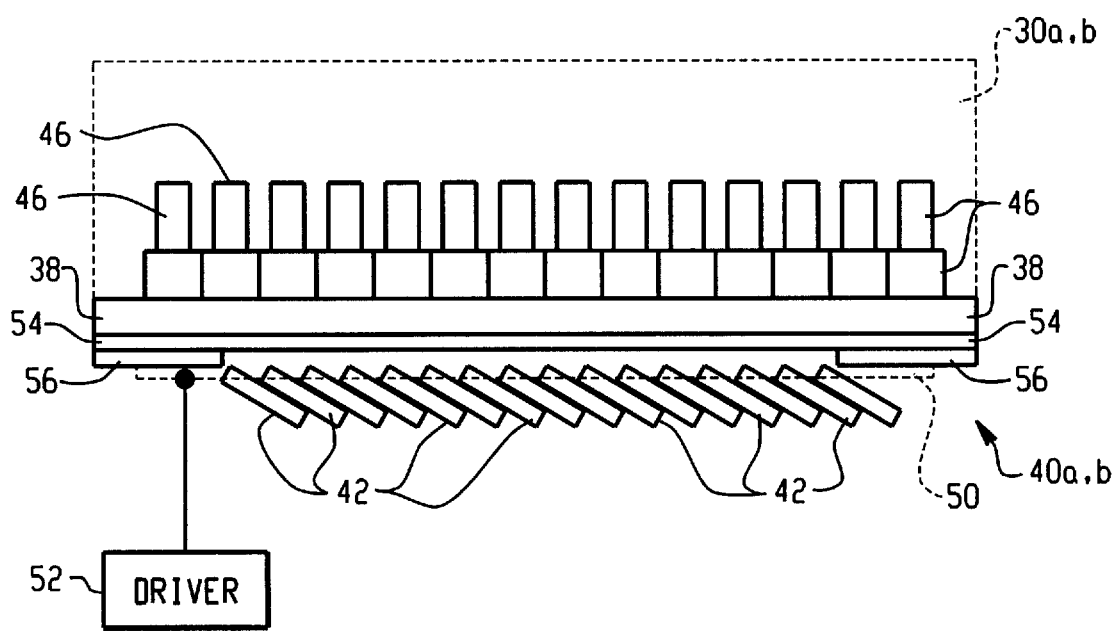
FIG. 3 is a diagrammatic illustration of a nuclear detector head employing a variable axial radiation shield in a radiation shielding mode in accordance with the present invention.

With reference to FIG. 3 and continuing reference to FIG. 2, the variable axial radiation shield 30a, 30b is shown with the plurality of vanes 42 oriented substantially parallel to the scintillator 38 in a radiation shielding mode. In the radiation shielding mode, high energy radiation events originating from the x-ray source or other transmission source are completely blocked from reaching the scintillation crystal 38. In other words, the plurality of substantially parallel vanes 42, which serve as the variable axial radiation shield, are pivotally closed in a venetian blind fashion, as shown in FIG. 3. The variable axial radiation shield is moved to the radiation shielding mode during the computed tomography or transmission portion of the diagnostic imaging sequence in order to block impermissibly high energy events from reaching the scintillation crystal.

The variable axial radiation shield 30a, 30b includes means 50 for pivoting the plurality of substantially parallel vanes 42 from an orientation substantially perpendicular to the scintillator 38 to an orientation substantially parallel to the scintillator 38. Exemplary means 50 includes a slide bar and a plurality of hinges or other pivot mechanism on each vane 42. The slide bar 50 is controlled by a driver 52 to open and close the vanes in a venetian blind fashion. It is to be appreciated that other mechanical devices may be employed to pivot the vanes from the radiation collimating mode to the radiation shielding mode.

The variable axial radiation shield 30a, 30b preferably includes a scatter shield 54, which is disposed between the scintillator 38 and the plurality of substantially parallel vanes 42, as shown in FIGS. 2 and 3. In addition, field-of-view limiting shielding 56 is disposed around the perimeter of the scintillator 56 in order to limit the field of view of the detector as desired. It is to be appreciated that the plurality of parallel vanes may be of uniform or variable spacing and pitch depending upon the particular diagnostic application.

Referring back to FIG. 1, when emission radiation from the subject and transmission radiation from the x-ray source are received by the nuclear detector heads 30a, 30b and x-ray detector 26, respectively, emission projection data and transmission projection data are generated. The emission data often contains inaccuracies caused by varying absorption characteristics of the subject's anatomy. The data is stored in either an emission data memory 62 or a CT data memory 64. A first reconstruction processor 66 reconstructs the collected transmission data, using an appropriate CT reconstruction algorithm, into a transmission image representation. From the reconstructed transmission image representation, an array of attenuation factors are determined and stored in an attenuation factor memory 68. Each voxel value stored in the attenuation factor memory 68 is indicative of attenuation of radiation by tissue in a corresponding volume within the subject 12.

An emission data trajectory processor 70 determines the trajectory of each emission data ray relative to the volumetric image representation in the attenuation factor memory and causes the attenuation values along the ray to be retrieved. An emission data correction processor 72 corrects the emission data in accordance with the attenuation factors determined from the CT data. More specifically, for each ray along which emission data is received, the emission data trajectory processor 70 calculates a corresponding ray through the attenuation factor array stored in the attenuation factor memory 68. Each ray of the emission data is then weighted or corrected by the emission data correction processor 72 in accordance with the attenuation factors.

The corrected emission data is reconstructed by a second reconstruction processor 74 in order to generate a three-dimensional emission image representation. The three-dimensional emission image representation is them combined or fused with the CT volumetric image representation by way of a combination processor 80. It is to be appreciated that the combined or fused image representation provides functional anatomical mapping. The fused or combined image representation is stored in a volumetric image memory 82. A video processor 84 withdraws selected portions of the data from the. image memory 82 to generate corresponding human-readable displays on a video monitor 86. Typical displays include reprojections, selected slices or planes, surface renderings, and the like.

Figure 4:
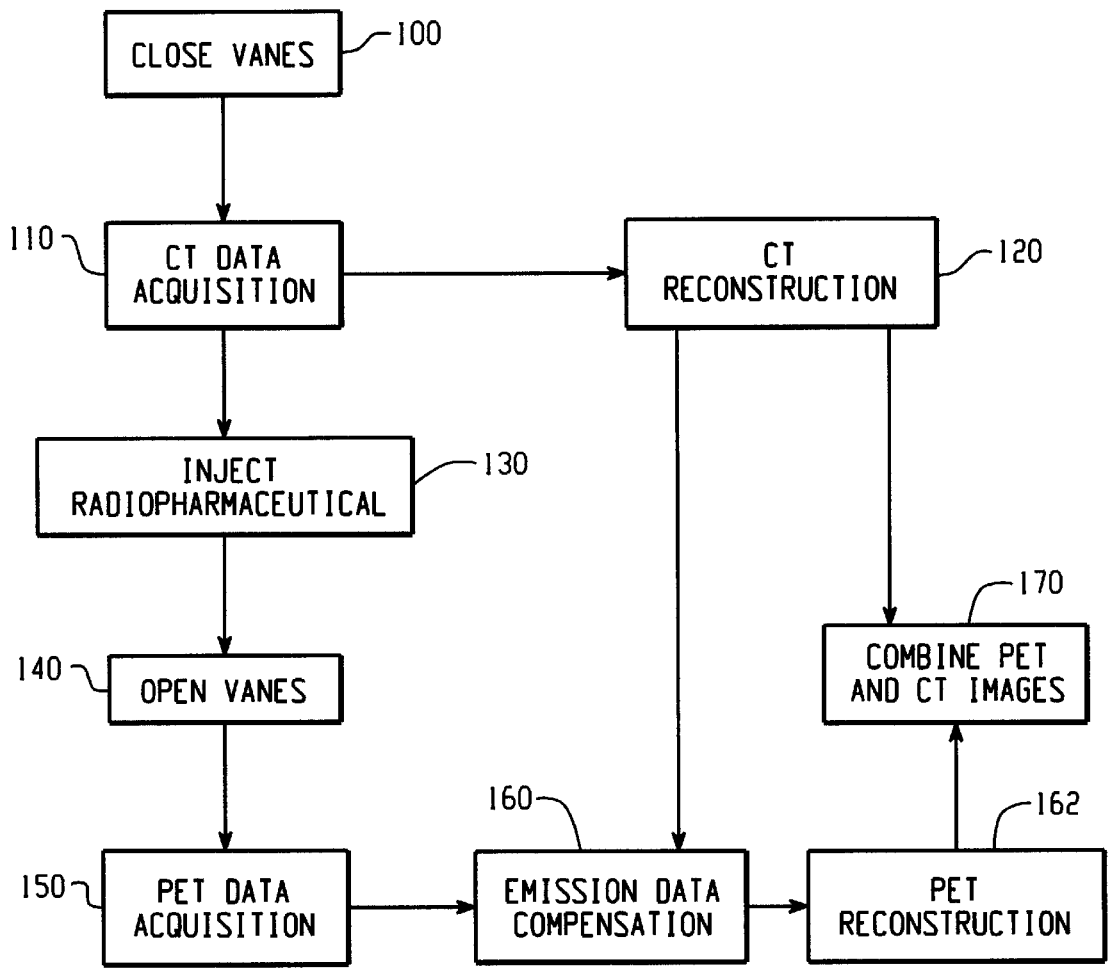
FIG. 4 is a flow chart illustrating a method of diagnostic imaging in accordance with the present invention.

With reference to FIG. 4 and continuing reference to FIG. 1, a method of diagnostic imaging illustrated using the diagnostic imaging system of FIG. 1 is provided. More particularly, the diagnostic imaging method relates to a combined PET/CT scanning technique involving the injection of a radiopharmaceutical, which is selectively absorbed by tumors or other tissues of interest. It is to be appreciated that the resultant PET image provides an accurate depiction of the location of the tumor or other tissue of interest in space. However, because only the radiopharmaceutical is imaged, the PET image provides little, if any, correlation between the image and the surrounding tissue. In order to coordinate the tumors or other regions of interest with surrounding tissue, the same region of the subject is scanned in a CT mode as well.

The plurality of substantially parallel vanes 42 contained within the variable axial radiation shield 30a, 30b are initially closed 100. In other words, the plurality of substantially parallel vanes are pivoted or otherwise translated such that they are oriented generally parallel to the scintillator 38 or in another orientation that blocks scattered radiation from reaching the scintillator. For example, odd vanes could tip one way and even vanes the other until the vanes touch at their leading and trailing edges. This mode protects the scintillator from high energy radiation events originating from the x-ray source or other source of penetrating radiation. Once the vanes of the variable axial radiation shield are closed in the radiation shielding mode, a CT data acquisition is performed 110. More particularly, x-ray radiation is transmitted from the x-ray source through the subject and toward the corresponding x-ray detector positioned across the subject receiving aperture. This x-ray data is then reconstructed 120 using a standard CT reconstruction, such as fan beam reconstruction or a volume cone beam reconstruction. If the CT and nuclear heads are axially offset, the patient is indexed axially to shift the region of interest from the CT examination region to the gamma camera examination region. Upon completion of the CT data acquisition 110, the subject is injected 130 with a radiopharmaceutical. If the uptake time is long compared to the CT scan time, the radiopharmaceutical can be injected prior to the CT scan. Once equilibrium is reached with regard to the radiopharmaceutical, the plurality of substantially parallel vanes are pivoted or otherwise moved 140 such that they are oriented substantially perpendicular to the scintillator in a radiation collimating mode. In the radiation collimating mode, non-axial radiation events are blocked or otherwise impeded from reaching the scintillator.

The emission data is corrected for subject attenuation 160 and reconstructed 162 into a corresponding emission data representation, which is then combined 170 with the CT or transmission image representation to form a combined or fused volumetric image representation.

It is to be appreciated that the variable axial radiation shield may be employed on a variety of nuclear detector systems and in conjunction with a variety of diagnostic imaging applications. In one embodiment, the variable axial radiation shield is employed on each nuclear detector head of a dedicated PET imaging system in which a plurality of nuclear detector heads are positioned around the subject receiving aperture.

The variable axial radiation shield also finds application in conjunction with cardiac imaging applications using short-lived radiopharmaceuticals, such as $^{82}$Ru. Cardiac imaging using $^{82}$Ru requires the patient to be continuously infused with the radiotracer for a period of time until equilibrium is reached within the cardiac anatomy. During the continuous infusion period, the patient is positioned within the subject receiving aperture, in front of the nuclear detector heads, exposing the nuclear detectors to a continuous high rate event. Without the use of the variable axial radiation shields on each detector head, detector saturation and compromised counting efficiency pan result. In this diagnostic application, the vanes of the variable axial radiation shields are closed or partially closed in a radiation shielding mode until radiotracer equilibrium is reached. Once equilibrium is reached, the vanes of the variable axial radiation shields are opened into a radiation collimating mode and the nuclear data is collected and processed.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system comprising:
   a stationary gantry which defines a subject receiving aperture;
   a rotating gantry mounted for rotation around the stationary gantry subject receiving region;
   a transmission radiation source which transmits radiation through a subject disposed in a subject receiving region, the transmission radiation source being mounted to the rotating gantry for rotation therewith;
   a transmission radiation detector for detecting the transmission radiation transmitted by the source after passage of the radiation through a transverse imaging slab of the subject in the subject receiving region, the transmission radiation detector being mounted to the rotating gantry for rotation therewith;
   at least one nuclear detector head mounted to the rotating gantry for rotation around the subject receiving region, which detector head detects emission radiation emitted from within the transverse imaging slab by a radiopharmaceutical injected into the subject, wherein each nuclear detector head including;
      a planar scintillation crystal which emits a short duration light scintillation in response to radiopharmaceutical emission radiation incident thereon and which glows emitting light for a longer duration in response to scattered transmission radiation;
      a plurality of opto-electrical elements optically coupled to the scintillation crystal, said opto-electrical elements converting light received from the scintillation into a plurality of electrical output signals; and
      a variable axial radiation shield disposed adjacent the scintillation crystal, said variable axial radiation shield shielding the scintillation crystal from (i) scattered emission radiation originating from the injected radiopharmaceutical and (ii) the transmission radiation originating from the transmission radiation source; and
      at least one reconstruction processor which reconstructs the transmission radiation received by the transmission radiation detector and the radiopharmaceutical emission radiation received by the nuclear detector head into volumetric image representations.

2. The diagnostic imaging system according to claim 1, wherein the variable axial radiation shield includes:
   a plurality of substantially parallel vanes movably mounted adjacent the scintillation crystal.

3. A diagnostic imaging system comprising:
   a stationary gantry which defines a subject receiving aperture;
   a transmission radiation source which transmits radiation through a subject disposed in a subject receiving region, the transmission radiation source being mounted for rotation around the stationary gantry subject receiving region;

a radiation detector for detecting the transmission radiation transmitted by the transmission radiation source after passage of the transmission radiation through the subject in the subject receiving region;

at least one nuclear detector head mounted for rotation around the subject receiving region, which detector head has a planar radiation receiving face through which emission radiation emitted by a radiopharmaceutical injected into the subject is received;

a plurality of substantially Parallel vanes pivotally mounted across the planar radiation receiving face of the nuclear detector head;

a means for pivoting the plurality of substantially parallel vanes between an open orientation substantially perpendicular to the planar radiation receiving face of the nuclear detector head and a closed orientation substantially parallel to the planar radiation receiving face to block radiation from being received;

at least one reconstruction processor which reconstructs the transmission radiation received by the transmission radiation detector and the emission radiation received by the nuclear detector head into volumetric image representations.

4. The diagnostic imaging system according to claim 3, further comprising:

an attenuation correction processor for correcting emission data from the nuclear detector head in accordance with the reconstructed volumetric transmission representation.

5. The diagnostic imaging system according to claim 2, wherein the variable axial radiation shield further includes:

a field-of-view limiting radiation shield disposed around a perimeter of the scintillation crystal; and a scatter shield disposed between the scintillation crystal and the plurality of vanes.

6. The diagnostic imaging system according to claim 2, wherein the plurality of vanes are uniformly spaced.

7. The diagnostic imaging system according to claim 2, wherein the at least one nuclear detector head includes:

a pair of detector heads spaced opposite each other across the subject receiving region for coincidence detection.

8. A diagnostic imaging system comprising:

a stationary gantry which defines a subject receiving aperture;

a transmission radiation source of penetrating radiation which transmits radiation through a subject disposed in a subject receiving region, the transmission radiation source being mounted for rotation around the stationary gantry subject receiving region;

a transmission radiation detector for detecting the transmission radiation from the transmission radiation source after passage of the transmission radiation through the subject in the subject receiving region;

a plurality of radiation opaque plates that are movable between an open configuration in which emission radiation is received by a nuclear detector head and a closed configuration in which the emission and transmission radiation are blocked by the plates from being received by the nuclear detector heads;

at least one nuclear detector head mounted for rotation around the subject receiving region, which detector head detects emission radiation emitted by a radiopharmaceutical injected into the subject;

at least one reconstruction processor which reconstructs transmission radiation received by the transmission radiation detector and the emission radiation received by the nuclear detector head into volumetric image representations;

a fusion processor which combines the transmission and emission radiation volumetric image representations together.

9. The diagnostic imaging system according to claim 8, wherein the plates are disposed perpendicular to and across a radiation receiving face of the detector head in the open configuration to allow the emission radiation to be received therebetween.

10. The diagnostic imaging system according to claim 9, wherein the plates are moved into contact with each other in the closed configuration.

11. The diagnostic imaging system according to claim 8, wherein the plates are disposed generally parallel to a radiation receiving face of the detector head in the closed configuration.

12. In a diagnostic imaging system having a rotating gantry which defines a subject receiving aperture, a source of penetrating transmission radiation and a corresponding transmission radiation detector means for generating a computed tomographic image representation of a subject disposed within the subject receiving aperture, a plurality of nuclear detector heads rotatably mounted to the rotating gantry, said detector heads each having an emission radiation receiving face and a variable radiation filter for selectively restricting transmission radiation from and permitting emission radiation to strike the radiation receiving face, the variable radiation filter including a plurality of vanes movably mounted across the radiation receiving face, a method of diagnostic imaging comprising:

positioning the plurality of vanes of the variable radiation filter such that they block radiation from striking the radiation receiving face of the nuclear detector heads;

transmitting the transmission radiation from the radiation source through the subject and toward the corresponding transmission detector means positioned across the subject receiving aperture while the vanes block the transmission radiation from striking the emission radiation receiving face of the nuclear detector heads;

reconstructing the transmitted radiation into a volumetric transmission image representation;

injecting a radiopharmaceutical into the subject disposed within the subject receiving aperture;

positioning the plurality of vanes of the variable radiation filter such that emission radiation emitted by the radiopharmaceutical is receivable by the radiation receiving face of the nuclear detector heads;

detecting the emission radiation emitted by the radiopharmaceutical;

reconstructing the detected emission radiation into an emission image representation; and combining the reconstructed volumetric transmission and emission image representations into a combined image representation.

13. The method according to claim 12, wherein the step of positioning the plurality of vanes of the variable radiation filter such that they block radiation from striking the radiation receiving face comprises:

positioning the plurality of vanes such that they are substantially parallel to the radiation receiving face.

14. In a diagnostic imaging system having a rotating gantry which defines a subject receiving aperture, a source of penetrating radiation and a corresponding detector means for generating a computed tomographic image representation of a subject disposed within the subject receiving aperture, a plurality of nuclear detector heads mounted to the rotating gantry, said detector heads each having a radiation receiving face and a variable radiation filter for selectively restricting and permitting radiation to strike the radiation receiving face, the variable radiation filter including a plurality of vanes movably mounted across the radiation receiving face, a method of diagnostic imaging comprising:

positioning the plurality of vanes such that they are substantially parallel to the radiation receiving face such that they block radiation from striking the radiation receiving face;

transmitting radiation from the radiation source through the subject and toward the corresponding detector means positioned across the subject receiving aperture;

reconstructing the transmitted radiation into a volumetric image representation;

injecting a radiopharmaceutical into the subject disposed within the subject receiving aperture;

positioning the plurality of vanes such that they are substantially perpendicular to the radiation receiving face such that radiation emitted by the radiopharmaceutical is receivable by the radiation receiving face;

detecting radiation emitted by the radiopharmaceutical;

reconstructing the detected emission radiation into an emission image representation.

15. The method according to claim 12, wherein the step of reconstructing the detected emission radiation includes:

calculating a plurality of attenuation factors from the volumetric transmission image representation; and correcting the emission radiation data based on the plurality of calculated attenuation factors.

\* \* \* \* \*